United States Patent
Yamamoto

(10) Patent No.: US 8,360,231 B2
(45) Date of Patent: Jan. 29, 2013

(54) METHOD AND APPARATUS FOR TRANSFERRING ARTICLES OF DIFFERENT SIZES

(75) Inventor: Yoichiro Yamamoto, Cologne (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/600,278

(22) Filed: Aug. 31, 2012

(65) Prior Publication Data
US 2012/0318641 A1  Dec. 20, 2012

Related U.S. Application Data

(63) Continuation of application No. 13/183,490, filed on Jul. 15, 2011, now Pat. No. 8,276,745.

(60) Provisional application No. 61/364,626, filed on Jul. 15, 2010.

(51) Int. Cl.
*B65G 37/00* (2006.01)
(52) U.S. Cl. ................ 198/623; 198/461.1
(58) Field of Classification Search .......... 198/623, 198/461.1, 626.1, 626.3, 461.2
See application file for complete search history.

(56) References Cited

U.S. PATENT DOCUMENTS

| | | | |
|---|---|---|---|
| 2,580,469 A * | 1/1952 | Schwartz | 198/623 |
| 2,935,916 A * | 5/1960 | Walker | 198/623 |
| 4,940,464 A | 7/1990 | Van Gompel et al. | |
| 5,092,861 A | 3/1992 | Nomura et al. | |
| 5,167,897 A | 12/1992 | Weber et al. | |
| 5,246,433 A | 9/1993 | Hasse et al. | |
| 5,360,420 A | 11/1994 | Cook et al. | |
| 5,569,234 A | 10/1996 | Buell et al. | |
| 5,599,335 A | 2/1997 | Goldman et al. | |
| 5,643,588 A | 7/1997 | Roe et al. | |
| 5,674,216 A | 10/1997 | Buell et al. | |
| 5,702,551 A | 12/1997 | Huber et al. | |
| 5,897,545 A | 4/1999 | Kline et al. | |
| 5,904,802 A | 5/1999 | Niedermeyer | |
| 5,957,908 A | 9/1999 | Kline et al. | |
| 5,968,025 A | 10/1999 | Roe et al. | |
| 6,107,537 A | 8/2000 | Elder et al. | |
| 6,118,041 A | 9/2000 | Roe et al. | |
| 6,120,487 A | 9/2000 | Ashton | |
| 6,120,489 A | 9/2000 | Johnson et al. | |
| 6,153,209 A | 11/2000 | Vega et al. | |
| 6,410,129 B2 | 6/2002 | Zhang et al. | |

(Continued)

FOREIGN PATENT DOCUMENTS

| | | |
|---|---|---|
| EP | 1 595 517 A1 | 11/2005 |
| EP | 1 726 278 A1 | 11/2006 |

(Continued)

OTHER PUBLICATIONS

PCT International Search Report and Written Opinion, dated Jun. 20, 2011, 13 pages.

(Continued)

*Primary Examiner* — James R Bidwell
(74) *Attorney, Agent, or Firm* — Abbey A. Lopez

(57) ABSTRACT

Method and apparatus for transferring articles from a first carrier moving at a first speed to a carrier moving at a second speed. The apparatus may include a first transfer surface driven by a first motor and second transfer surface driven by a second motor. The first and second transfer surfaces receive and transfer different portions of an article at different speeds such that a desired amount of spacing can be provided between discrete articles in a process independent of the size of the article.

7 Claims, 8 Drawing Sheets

U.S. PATENT DOCUMENTS

| | | |
|---|---|---|
| 6,426,444 B2 | 7/2002 | Roe et al. |
| 6,513,221 B2 | 2/2003 | Vogt et al. |
| 6,586,652 B1 | 7/2003 | Roe et al. |
| 6,617,016 B2 | 9/2003 | Zhang et al. |
| 6,627,787 B1 | 9/2003 | Roe et al. |
| 6,705,453 B2 | 3/2004 | Blumenthal et al. |
| 6,825,393 B2 | 11/2004 | Roe et al. |
| 6,861,571 B1 | 3/2005 | Roe et al. |
| 6,888,143 B2 | 5/2005 | Vogt et al. |
| 7,399,266 B2 | 7/2008 | Aiolfi et al. |
| 2002/0103468 A1 | 8/2002 | Nakakado et al. |
| 2003/0233082 A1 | 12/2003 | Kline et al. |
| 2006/0276320 A1 | 12/2006 | Aiolfi et al. |
| 2009/0094941 A1 | 4/2009 | Burns et al. |
| 2009/0098995 A1 | 4/2009 | Burns et al. |
| 2012/0228091 A1* | 9/2012 | Prati .............................. 198/623 |

FOREIGN PATENT DOCUMENTS

| | | |
|---|---|---|
| EP | 1 941 854 A2 | 7/2008 |
| WO | WO 95/19752 A2 | 7/1995 |
| WO | WO 2007/029195 A2 | 3/2007 |
| WO | WO 2008/001209 A2 | 1/2008 |
| WO | WO 2009/032995 A1 | 3/2009 |
| WO | WO 2009/083788 A1 | 7/2009 |

OTHER PUBLICATIONS

PCT International Search Report dated Oct. 28, 2011, 12 pages.
PCT International Search Report dated Aug. 30, 2011, 11 pages.
PCT International Search Report dated Sep. 27, 2011, 10 pages.
U.S. Appl. No. 13/183,481, filed Jul. 15, 2011, Yoichiro Yamamoto.
U.S. Appl. No. 13/183,483, filed Jul. 15, 2011, Yoichiro Yamamoto.
U.S. Appl. No. 13/183,486, filed Jul. 15, 2011, Yoichiro Yamamoto.
U.S. Appl. No. 13/051,210, filed Mar. 18, 2011, Yoichiro Yamamoto.

* cited by examiner

METHOD AND APPARATUS FOR TRANSFERRING ARTICLES OF DIFFERENT SIZES

CROSS REFERENCE TO RELATED APPLICATIONS

This application is a continuation of U.S. patent application Ser. No. 13/183,490, filed on Jul. 15, 2011, now U.S. Pat. No. 8,276,745 which claims the benefit of U.S. Provisional Application No. 61/364,626, filed on Jul. 15, 2010, each of which is herein incorporated by reference in its entirety.

FIELD OF THE INVENTION

The present disclosure relates to methods and apparatuses for transferring discrete articles between carriers, and more particularly, methods and apparatuses that change the speeds of different portions of an article relative to each other while transferring the article from one carrier to another carrier.

BACKGROUND OF THE INVENTION

Disposable absorbent articles, such as diapers, pull-on diapers, training pants, adult incontinence pads, wipes, facial tissue, toilet tissue, napkins, paper towels and the like are often manufactured and/or packaged on a high-speed production line (e.g., greater than 400 articles per minute) where individual articles may move along a production path at a speed of hundreds of meters per minute. It is not uncommon for such high-speed manufacturing processes to utilize conveyors and/or rolls to transfer articles from one process or process component to another. It is also not uncommon for the various transfer conveyors or rolls to operate at different speeds depending on the particular process involved. In order to minimize the potential risk of articles overwhelming the process equipment capability (e.g., causing undesirable errors associated with article detection equipment/sensors such automated vision systems/cameras, portions of the articles overlapping one another, and/or not providing sufficient time for certain components to properly reposition/reset for processing a subsequent article in a series of articles), the articles are typically spaced apart from one another at least in the machine direction.

Disposable absorbent articles such as children's diapers, training pants, and the like are typically sold in a variety of sizes based on, e.g., the weight and/or age of the child who wears the article, and the size difference in such articles typically translates to a difference in the overall length of the articles (i.e., larger sized articles are typically longer than smaller sized articles). In certain processes such as conventional diaper or pant making processes, when the manufacturer chooses to make a different size of article, certain components of the manufacturing process may not provide a suitable amount of spacing between articles when the length of the article is changed (e.g., the transfer conveyor and/or drum). In order to address problem of making different sized article sizes, at least some manufacturers keep different sized conveyors/rolls on hand. Thus, when the article size is changed, the conveyor or roll is replaced with one that is tailored to accommodate the desired article size. Not surprisingly, stopping the manufacturing line to replace a conveyor/roll may result in an undesirable loss of production time.

Accordingly, it would be desirable to provide a process and apparatus for transferring articles of different sizes from one carrier to another without having to replace a carrier.

SUMMARY OF THE INVENTION

In order to provide a solution to the problems above, at least one embodiment discloses an apparatus for transferring articles in a machine direction from a first carrier moving at a first speed to a second carrier moving at a second speed that is greater than the first speed. Each article has a leading end portion and a trailing end portion. The apparatus comprises a first transferring surface configured to receive the leading end portion of each article from the first carrier and transport the leading end portion of each article to the second carrier. The first transferring surface is mechanically coupled to a first drive motor that advances the first transferring surface in the machine direction. The apparatus also comprises a second transferring surface configured to receive the trailing end portion of each article from the first carrier and transport the trailing end portion of each article to the second carrier. The second transferring surface is mechanically coupled to a second drive motor that advances the second transferring surface in the machine direction. The first drive motor is configured to advance the first transferring surface at the first speed when the leading end portion of each article is transferred from the first carrier to the first transferring surface, decelerate the first transferring surface to accumulate slack in the article, and accelerate the first transferring surface back to the second speed such that the leading end portion of the article is transferred to the second carrier at the second speed. The second drive motor is configured to advance the second transferring surface at the first speed when the trailing end portion of each article is transferred from the first carrier to the second transferring surface and accelerate the second transferring surface to the second speed such that the trailing end portion of each article is transferred to the second carrier at the second speed.

DETAILED DESCRIPTION OF THE INVENTION

Figure 1:
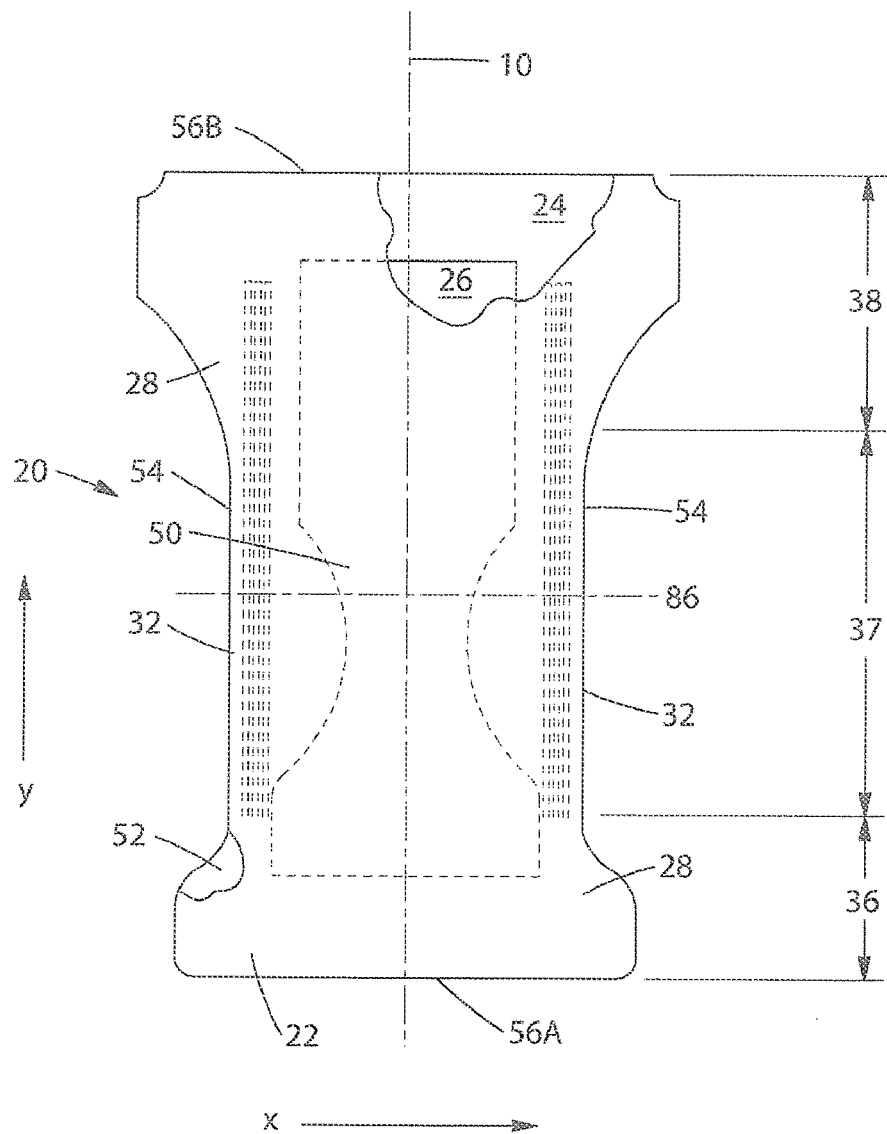
FIG. 1 is a top, plan view of a disposable absorbent article.

"Absorbent article" means a consumer product whose primary function is to absorb and retain soils and wastes, such as devices which are placed against or in proximity to the body of the wearer to absorb and contain the various exudates discharged from the body. Wearable Nonlimiting examples of absorbent articles include diapers, training pants, pull-on pant-type diapers, refastenable diapers or pant-type diapers, incontinence briefs and undergarments, diaper holders and liners, feminine hygiene garments such as panty liners, absorbent inserts, and the like.

"Aligned" means an article in a bifold configuration having an average CD accuracy and an MD accuracy of less than or equal to 3 mm, when measured according to the Alignment Test described in copending U.S. Publication. No. 2009/0098995, titled "System For Bifolding An Absorbent Article," filed by Burns, et al.

"Bifold" means folding an article into two portions. For example, bifolding a disposable diaper may be accomplished by bringing the leading end and the trailing end of the diaper together in a face-to-face configuration on a production line as the article moves in the machine direction of travel, such that the diaper is folded along a fold line into two substantially equal portions. As used herein, a "fold line" is the portion of an article about which the article is folded. The fold line typically extends from one side edge to the opposing side edge in the crotch region and, in certain embodiments, may correspond to the lateral centerline of the article. In certain embodiments, the leading end edge and trailing end edge of an article may be aligned after the article is folded.

"Diaper" or "taped diaper" mean disposable absorbent articles having an initial front waist region and an initial back waist region that are not fastened, pre-fastened, or connected to each other as packaged, prior to being applied to the wearer. A taped diaper is folded about the lateral centerline with the interior of one waist region in surface to surface contact with the interior of the opposing waist region without fastening or joining the waist regions together. Suitable taped diapers are disclosed in various suitable configurations are disclosed in U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571.

"Disposable" means articles that are generally not intended to be laundered or otherwise restored or reused as absorbent articles (i.e., they are intended to be discarded after a single use and may be recycled, composted or otherwise discarded in an environmentally compatible manner).

"Disposed" means an element(s) is formed (joined and positioned) in a particular place or position as a macro-unitary structure with other elements or as a separate element joined to another element.

"Engage," when used in the context of transferring an article from one carrier to another or from a portion of one carrier to another portion of the same carrier, means coming into close proximity (e.g., <10 cm, up to and including physical contact) such that an engaging force (e.g., suction) present at the surface of the carrier can be applied to an article.

"Holding an article to the surface of a roll" and variations thereof mean employing a holding force to one or more portions of an article in order to join the article at least temporarily to the surface of a roll such that the article is inhibited from traveling in a direction substantially orthogonal to the surface of the roll without reducing or removing the holding force and/or employing a peel-force. This definition is equally applicable to conveyors, e.g., one or more of the conveyor assemblies described hereinbelow.

"Joined" means configurations whereby an element is directly secured to another element by affixing the element directly to the other element and to configurations whereby an element is indirectly secured to another element by affixing the element to intermediate member(s) which in turn are affixed to the other element.

"Longitudinal" means a direction running substantially perpendicular from a waist edge to an opposing waist edge of an absorbent article when the article is in a flat out, uncontracted state, or from a waist edge to the bottom of the crotch in a bifolded article. Directions within 45 degrees of the longitudinal direction are considered to be "longitudinal." "Lateral" refers to a direction running from a longitudinal edge to an opposing longitudinal edge of an article and generally orthogonal to the longitudinal direction. Directions within 45 degrees of the lateral direction are considered to be "lateral."

"Machine direction" ("MD") means the direction that is parallel to the direction of travel of an article or article element as it is processed in the forming apparatus. In a folding process such as a bifolding process, it may be possible to have more than one machine direction when an article is undergoing simultaneous processes. In other words, a manufacturing line may have an overall machine direction, but an article may travel in directions other than the overall machine direction as it passes through various process along the manufacturing line. For example, an article having a trailing end portion and a leading end portion, each portion being attached to the surface of a different roll and/or conveyor, may travel in two different directions simultaneously. In this example, both directions of travel may be considered the machine direction. The "cross machine direction" or "cross direction" ("CD") refers to the direction perpendicular to the machine direction and in the plane generally defined by the article or article element.

"Mechanically coupled" means two or more components that, directly or indirectly, act cooperatively to form a mechanism. For example, an electric motor that drives the motion of a gate is said to be mechanically coupled to the gate. The mechanism of operation that mechanically couples the component may be any one of a number of commonly known couplers, including but not limited to: having a shaft extending between the components; a universal joint; a transmission; a linkage; a sprocket and chain; a gear head on one of the components; a gear box; a belt and pulley combination; a clutch mechanism; a spring member; a slider; a pivot; or other known forms of coupling two elements may also be considered mechanical coupling.

"Mechanically secured" means holding an object in place by a mechanical means. For example, a web of material or an absorbent article held to the outer surface of a roll with clips is considered to be mechanically secured. Conversely, holding a web of material or an absorbent article to the surface of a roll with vacuum pressure or centrifugal force is not an example of being mechanically secured.

"Peel force" means the force applied to an object in a direction that is substantially perpendicular to the plane of the surface on which the object rests. A force applied in a direction within 45° of the perpendicular direction may be considered a peel force.

"Training pant(s)" or "pant(s)" mean disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by any suitable technique including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened, front waist fastened, rear waist fastened). Suitable examples of pants in various configurations are disclosed in U.S. Pat. Nos. 5,246,433; 5,569,234; 6,120,487; 6,120,489; 4,940,464; 5,092,861; 5,897,545; 5,957,908; and U.S. Patent Publication No. 2003/0233082.

"Vacuum" and "vacuum pressure" mean a pressure of less than 13,000 Newtons per square meter.

Aspects of the present disclosure involve methods and apparatuses for manufacturing articles, and more particularly, apparatuses and methods for transferring discrete articles from one carrier to another carrier, wherein the carriers operate at different speeds. It is to be understood that while one or more particular examples recited herein may refer to a diaper or training pant, the present invention is not limited to such articles, but may, in fact, be practiced to great advantage in any situation where an article exhibiting the characteristics described herein is required. Conventional processes and apparatuses typically maintain articles in a flat-out state throughout the manufacturing process. The apparatuses and methods herein utilize transferring devices that transport different regions of an article from a transfer apparatus moving at a first speed to a second carrier moving at a second speed different from the first speed, wherein the article is not constantly held in a flat-out state. In certain embodiments, a first transferring device may include a first transferring surface that receives a first region of an article from the transfer apparatus, and a second transferring device may include a second transferring surface that receives a second region of an article from the transfer apparatus. The first region and the second region may be separated by a third region of the article. For example, when transferring diapers, the first, second, and third regions may correspond with first waist, second waist, and crotch regions, respectively. The first transferring device transports the first region of the article to the second carrier, and the second transferring device transports the second region of the article to the second carrier. After receiving the first region from the transfer apparatus traveling at the first speed, the first transferring device may decelerate and/or accelerate the first transferring surface and first region from the first speed. And after receiving the second region from the transfer apparatus traveling at the first speed, the second transferring device may decelerate and/or accelerate the second transferring surface and second region from the first speed. The first region is then transferred from the first transferring device to the second carrier traveling at the second speed, and the second region is then transferred from the second transferring device to the second carrier traveling at the second speed.

FIG. 1 shows a partial cut-away view of a diaper 20 shown in a flat-out, uncontracted state (e.g., with no elastic induced contraction). The diaper 20 may include a body-faceable, liquid pervious topsheet 22 (i.e., faces and/or contacts the body of a wearer when worn as intended); a clothing-faceable, liquid impervious backsheet 24 joined with the topsheet 22 (i.e., faces and/or contacts the clothing of a wearer when worn as intended); an absorbent core 26 positioned between the topsheet 22 and the backsheet 24; side panels 28; and leg cuffs 32. The diaper 20 may further include an outer surface 52 opposed to the inner surface 50, a first waist region 36, a second waist region 38 opposed to the first waist region 36, and a crotch region 37 positioned between the first waist region 36 and the second waist region 38. The diaper 20 may also include longitudinal edges 54, a first end edge 56A corresponding to the first waist region 36, and an opposing second end edge 56B corresponding to the second waist region 38. The diaper 20 may include a longitudinal centerline 10 positioned midway between the longitudinal side edges 54 and a lateral centerline 86 positioned midway between opposing end edges 56A and 56B and orthogonal thereto. The end edges 56A and 56B may be substantially equal in width, as measured from opposing longitudinal side edges 54 to the longitudinal centerline 10, or length, as measured from opposing end edges 56A and 56B to the lateral centerline 86, in order to facilitate folding of the diaper 20, but need not necessarily be so. In some instances, it may be desirable to fold the diaper 20 about the lateral centerline 86 such that the first waist region 36 and the second waist region 38 are positioned in a face-to-face relationship along the inner surface 50 (e.g., in a bifolded configuration). Such a folded diaper may have the first end edge 56A and the second end edge 56B aligned. Additionally or alternatively, the folded diaper may have the longitudinal side edges 54 partially or entirely aligned (e.g., the longitudinal side edges 54 may be aligned only in those areas that are visible to a consumer and/or are to be permanently joined together).

Figure 2:
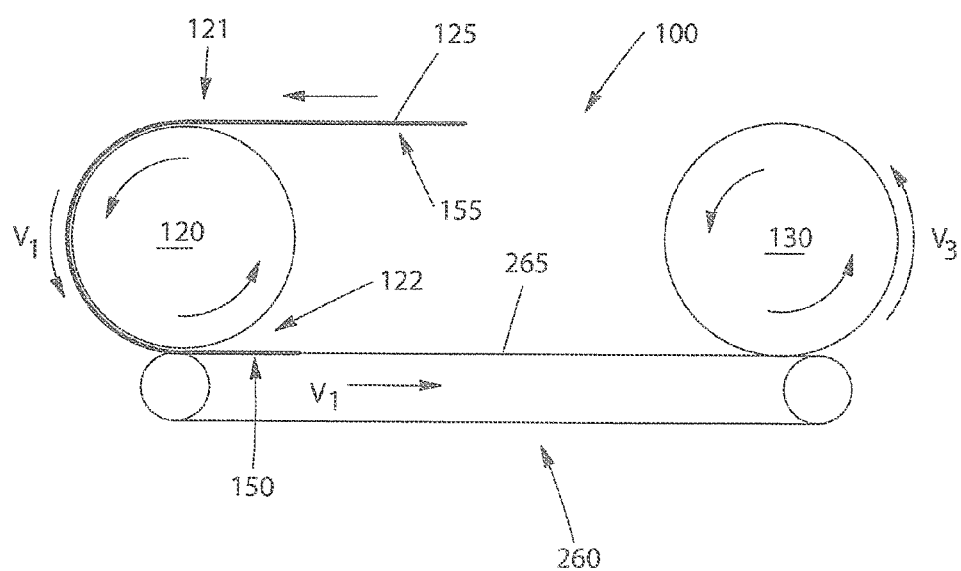
FIG. 2 is a schematic view of an embodiment of the method and apparatus disclosed herein.
Figure 3:
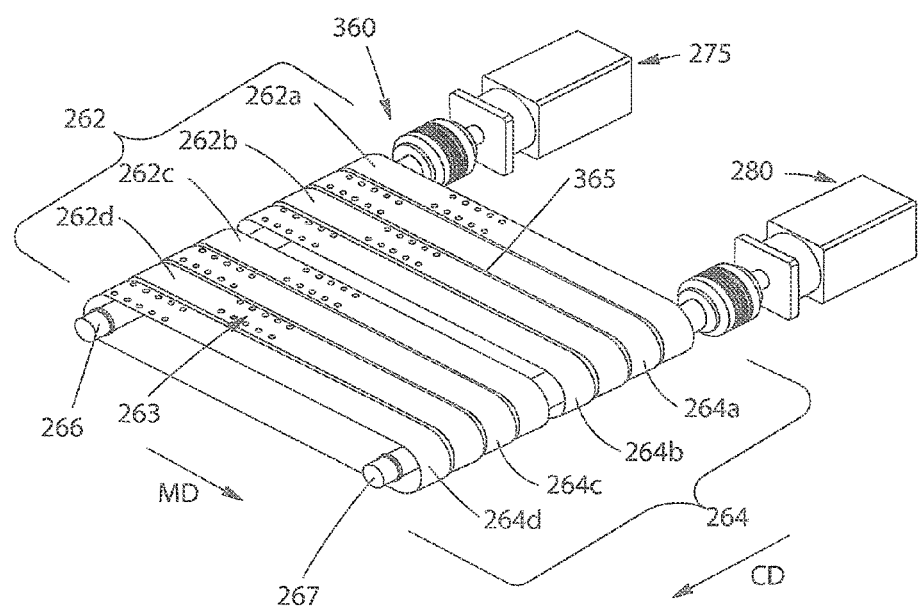
FIG. 3 is a perspective view of an embodiment of the apparatus disclosed herein.
Figure 4:
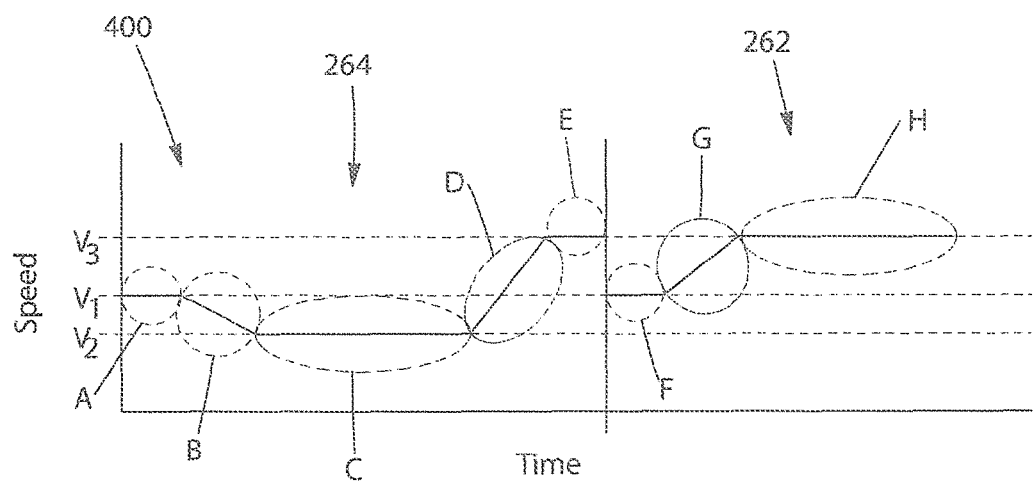
FIG. 4 is a graph illustrating a speed profile for the transfer apparatus of FIG. 3.

FIG. 2 shows an exemplary process 100 wherein absorbent articles are transferred from one carrier to another as they advance in the machine direction. Arrows are provided to indicate the direction of movement of particular components in the process 100. As illustrated in FIG. 2, an absorbent article 125 may be transported to the infeed 121 of a rotating first carrier 110 travelling at a first speed $V_1$. In the exemplary embodiment shown in FIG. 2, the first carrier 110 is depicted as being a roll, but it should be understood that the first carrier 110 may be replaced with a suitable conveyor, or any other suitable carrier known in the art that is configured to provide an endless moving surface. The absorbent article 125 may be held to the surface of the first carrier 120 to help secure the article 125 in a desired position and/or configuration. For example, the first carrier 120 may include a foraminous surface through which vacuum suction can be provided to hold the article 125 or article portions in place. In certain embodiments, the first carrier 120 may use a mechanical means such as clips or clamps to hold the article 125 or article portions in place. The method used to provide the holding force is not particularly limited as long as it does not undesirably interfere with the process 100. After being received by the first carrier 120, the absorbent article 125 is carried around the rotating surface of the first carrier 120 toward the transfer apparatus 260 at speed $V_1$. Upon reaching the outfeed 122 of the first carrier 120, the leading end 150 of the absorbent article 125 is transferred to the movable surface 265 of the transfer apparatus 260. The transfer apparatus 260 may be configured as one or more of the conveyors described in more detail below, or as a rotary drum that includes two or more independently rotating heads such as, for example, one of the rotary drums described copending U.S. Ser. No. 61/364,610, filed by Yamamoto, et al., on Jul. 15, 2010, titled "Apparatus And Method For Folding Articles.". Before, during, or after transfer of the absorbent article 125 or portion thereof, the holding force exerted by the first carrier 120, if any, may be reduced and/or removed. The transfer apparatus 260 carries the leading end 150 toward the infeed 131 of the second carrier 130, which is rotating at speed $V_3$, as shown in FIG. 4. The second carrier 130 may be a roll or belt, as desired. In certain embodiments, the second carrier may be a folding drum such as one or more of the folding drums described in U.S. Pub. No. 2009/0098995, filed by Burns, et al., on Sep. 4, 2008; U.S. Provisional Ser. No. 61/322,333; filed by Yamamoto, et al., on Apr. 9, 2010; and/or copending U.S. Ser. No. 61/364,616, filed by Yamamoto et al, on Jul. 15, 2010, titled "Apparatus and Method For Folding Articles." In certain embodiments, the article may be transferred to the second carrier 130 and subjected to one or more of the processes (e.g., folding, seaming) described in U.S. Publication No. 2009/0094941, filed by Burns, et al., on Sep. 3, 2008; and U.S. Pat. No. 6,888,143 to Vogt, et al. While the second carrier 130 is illustrated in the figures as being positioned on the same side of the transfer apparatus 260 as the first carrier 120, it is to be appreciated that the first and second carriers 120, 130 may be positioned on different sides of the transfer apparatus, for example, as depicted in copending U.S. Ser. No. 61/364,604, filed by Yamamoto, et al., on Jul. 15, 2010, titled "Method and Apparatus For Transporting and Folding Articles," and identified as P&G FIG. 3 shows an exemplary embodiment of a transfer apparatus 360 suitable for use herein. As shown in FIG. 3, the transfer apparatus 360 may be a conveyor with a belt configured in an endless loop to provide a movable surface 365. The movable surface 365 may include a first set of four individual belts 262a, 262b, 262c, 262d arranged in an alternating relationship with a second set of four individual belts 264a, 264b, 264c, 264d to form a substantially flat moveable surface. It is to be understood that the any number of individual belts (e.g., 2, 3, 5, 6, 7) or sets of belts may be used, as desired. For example, the transfer apparatus 360 may be configured to include 3 or even 4 or more sets of belts to accommodate a variety of cycle rates (e.g., two articles per complete cycle, one and half articles per cycle, or 1 article per cycle). The individual belts 262a-d, 264a-d may be the same size or different sizes, as long as the overall size of the set of belts 262, 264 is sufficient to suitably accommodate the desired article size. For example, each set of belts 262, 264 may be sized in the MD to accommodate the longest article in the line-up of absorbent articles provided by a manufacturer. In certain embodiments, the transfer apparatus 360 may transfer two articles each time the endless belt completes a full rotation around the loop, and may be referred to as a so-called "two-up" belt. The width of an individual belt or set of belts is not particularly limited as long as the width of each set of belts 262, 264 in the CD is sufficient to suitably accommodate the desired absorbent article sizes being produced. The individual belts 262a-d, 264a-d in each set of belts 262, 264 cooperatively function to advance a portion of an absorbent article in the MD without inhibiting the advancement of the remaining portions of the article. Thus, in certain embodiments, it may be desirable to hold a portion of the article to the surface or a portion of the surface of one or more of the belts 262a-d, 264a-d. For example, one or more of the belts 262a-d, 264a-d may be configured with one or more openings 263 that extend through the belt 262a-d, 264a-d to permit vacuum to be applied to an article or article portion disposed on the belt. It may be desirable, in certain embodiments, to configured the belts 262a-d, 264a-d such that the holding force (e.g., vacuum) does not undesirably inhibit the advancement of the article portion(s) disposed thereon. (e.g., by not placing holes 263 in portions of the belt 262a-d, 264a-d or by the intermittent application of vacuum).

Each set of belts 262, 264 may be driven independently by a drive motor 275, 280 or any other suitable prime mover known in the art (e.g., a variable speed, linear servo motor). A particularly suitable example of a drive motor is a programmable, variable speed, linear servo motor configured such that the coil and magnet assembly of the motor do not make contact, which reduces the amount of dust and/or other particulate contamination generated by the motor during operation and makes the motor more suitable for environments where cleanliness is desired (e.g., when making sanitary disposable articles that are used on or near skin) or where vacuum systems are utilized. In certain embodiments, one or more of the motors may be a constant speed motor. Each drive motor 275, 280 is mechanically coupled to its respective set of belts 262, 264, for example, by a shaft 266, 267 and one or more pulleys. In certain embodiments, each shaft may also be configured to function as a so-called "idler pulley" for the opposite set of driven belts, for example, by permitting the opposing set of belts to ride on a freely rotating (i.e., undriven) pulley mounted to the shaft with a roller bearing. For example, shaft 266 may be used to drive individual belts 262a-d, but function as an idler pulley for individual belts 264a-d.

FIG. 4 shows a graph 400 illustrating an exemplary speed profile for the transfer apparatus 360 of FIG. 3. As shown in FIG. 4, time is represented on the x-axis graph 400 and speed is represented on the y-axis. The broken line circles A-H represent various spans of time during the operation of the transfer apparatus 360. As described above, the transfer apparatus 360 includes a first set of belts 264 and a second set of belts 262 configured to transfer an article from a first carrier travelling at one speed ($V_1$ in this example) to a second carrier travelling at a different speed ($V_3$ in this example). At time A, the first set of belts 264 receives the leading end of an article at the first speed $V_i$. At time B, the first set of belts decelerates the leading end to speed $V_2$ to accumulate slack and provide space between the current article and the previous article. At time C, the first set of belts 264 advances the leading end in the MD at speed $V_2$ until the desired spacing is reached, during which time slack continues to accumulate in the article. At time D, the first set of belts accelerates to speed $V_3$ and advances the leading end toward the second carrier. At time E, the leading end is transferred to the second carrier at speed $V_3$. At time F, which may overlap time E depending on the spacing and cycle times desired, the second set of belts 262 receives the trailing end of the article at speed $V_1$. The second set of belts accelerates the trailing end to speed $V_3$ at time G. At time H, the trailing end is transferred to the second carrier at speed $V_3$.

Figure 5:
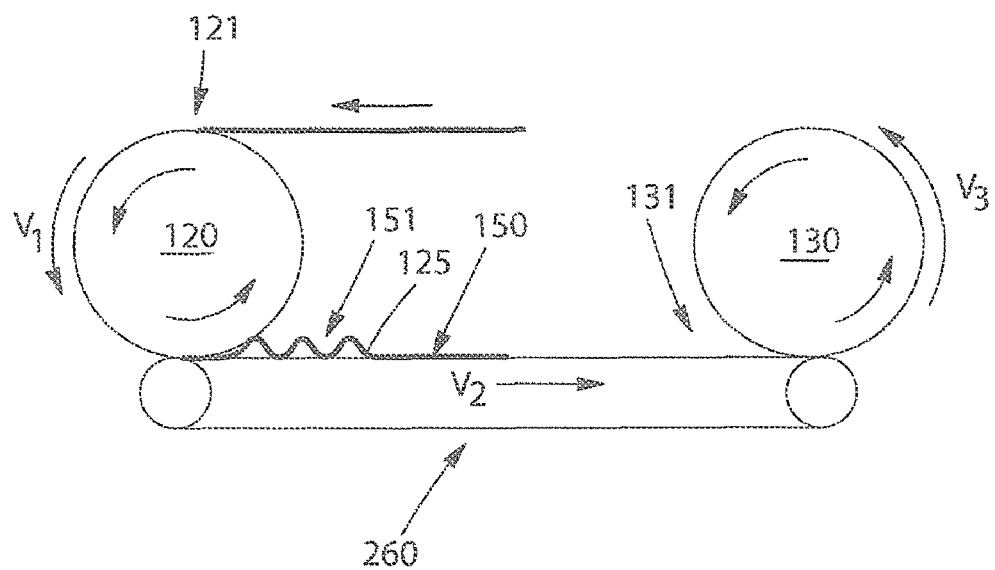
FIGS. 5-7 are schematic views of an embodiment of the method and apparatus disclosed herein.
Figure 6:
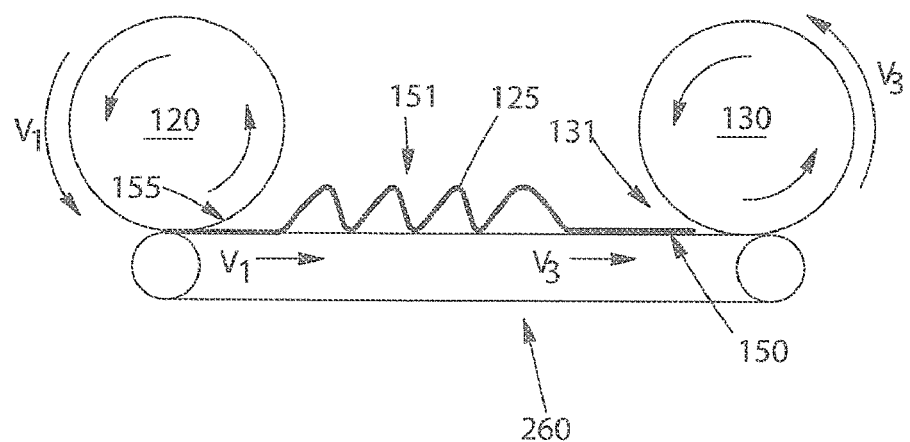

Referring to FIGS. 2 and 5-7, a description of an exemplary embodiment is provided. As the leading end 150 of the absorbent article 125 approaches the transfer apparatus 260 at a first speed $V_1$, the leading end 150 may be engaged by a first set of belts such as, for example, the first set of belts 264 shown in FIG. 3 by applying a peel force to the leading end 150. The first set of belts may then transport the leading end 250 away from the first carrier 120 toward the infeed 131 of the second carrier 130 in the MD at a second speed $V_2$, which is slower than the first speed $V_1$. Because the rate at which the leading end 150 is being carried away from the first carrier 120 is slower than the rate at which the absorbent article 125 is being fed to the transfer apparatus 260 (i.e., $V_2<V_i$), slack 151 may tend to accumulate in the portion of the article 125 between the trailing end 155 and the leading end 150 ("middle portion"). While the leading end 150 continues to advance in the MD toward the second carrier 130 at the second slower speed $V_2$, more of the absorbent article 125 is fed onto the transfer apparatus 260 at the first speed $V_i$, which causes further bunching, as illustrated in FIG. 5. Eventually, the trailing end 155 of the absorbent reaches the outfeed 122 of the first carrier 120 and is engaged by a second set of belts such as, for example, the second set of belts 262 shown in FIG. 3 at the first speed $V_1$. In certain embodiments (e.g., before or during the transfer of the trailing end 155 to the second set of belts), the first set of belts may be accelerated to speed $V_3$, which is greater than speed $V_1$, to begin removing at least some of the slack 151 in the article 125 and match the speed of the leading end 150 to the speed of the second carrier. The leading end 150 is transferred to the second carrier 130 at the third speed $V_3$. And the trailing end 155 is accelerated to the third speed $V_3$ prior to being transferred to the second carrier 130 (e.g., when all or most of the slack 151 is removed from the article 125, as shown in FIG. 6). Thus, the spacing between the trailing end of the previous absorbent article in the process 100 and the leading end 150 of the current absorbent article 125 can be desirably controlled by adjusting the acceleration/deceleration of the movable surface 265 of the transfer apparatus 260 belt without having to replace the carrier. As will be readily recognized by those skilled in the art, the spacing between articles can be suitably controlled independent of the size of the article. It is to be appreciated that, in certain embodiments, the article 125, including the trailing end portion 155, may be transferred to the second carrier 130 while at least some slack 151 remains in the article 125.

As can be readily discerned from the description and figures herein, there are a variety of configurations for accelerating and decelerating the various components described herein that may provide the benefit of transferring articles of different lengths from one carrier to another without replacing a carrier. For example, referring again to FIGS. 2 and 4-6, the leading end 150 may be transferred to the transfer apparatus 260 at the first speed $V_1$, but instead of decelerating the leading end 150, as described above, the speed of the leading end 150 may be kept substantially constant, e.g., at $V_1$. Then (e.g., before, during, or even after the transfer of the trailing end 155 to the second set of belts), the trailing edge 155 may be accelerated to a faster speed (e.g., $V_3$ or even faster), which creates slack 151 in the middle portion of the absorbent article 125 and, importantly, provides a suitable space between the trailing end 155 of the current article 125 and the leading end of a subsequent article in the process 100. The speed of the leading edge 150 may be simultaneously or subsequently increased to $V_3$ in preparation for transferring to the second carrier 130. Once the desired spacing between articles is obtained, the trailing end 155 may be decelerated in order to remove at least some of the slack 151 (i.e., the trailing end 155 is travelling slower than the leading end 150, e.g., less than speed $V_3$). Once some or all of the slack 151 is removed from the absorbent article 125 and/or if the trailing end 155 is not travelling at speed $V_3$, the speed of the trailing edge 155 may be adjusted to $V_3$ prior to transfer of the trailing end 155 to the second carrier 130.

Figure 7:
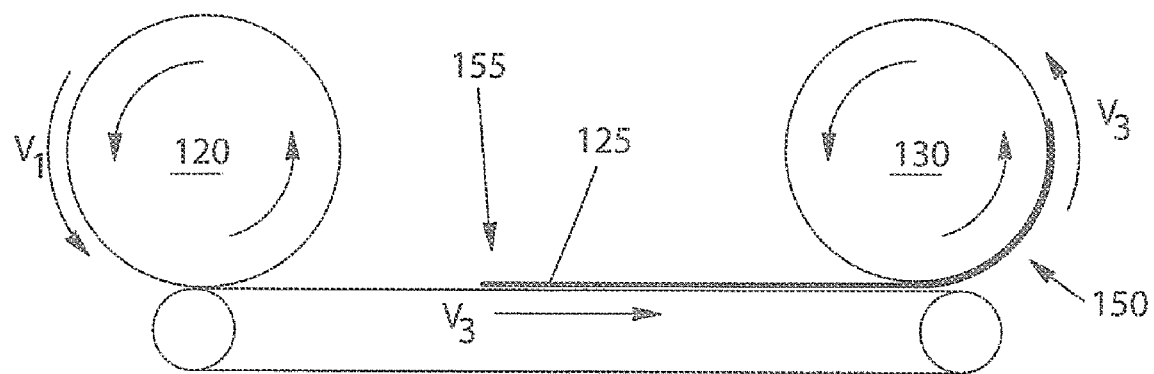
Figure 8:
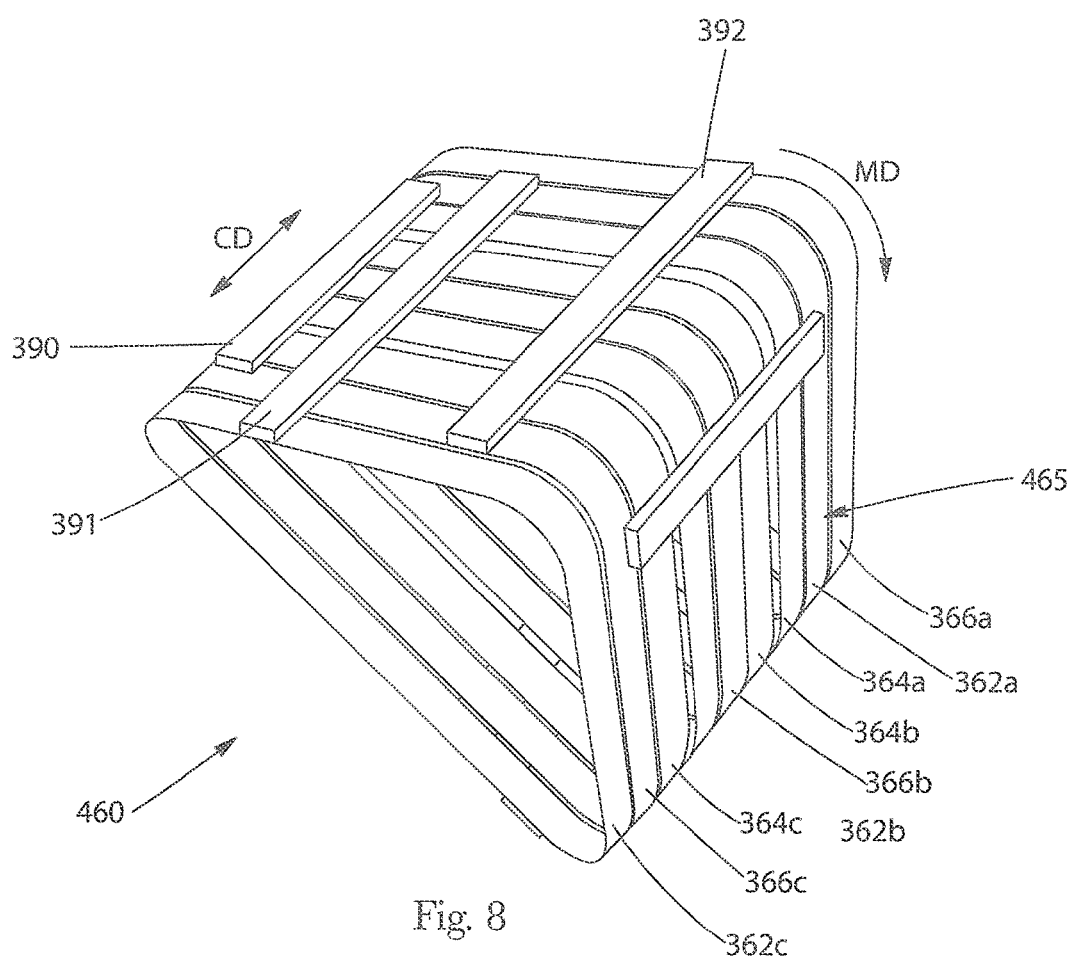
FIG. 8 is a perspective view of an embodiment of the apparatus disclosed herein.

FIG. 7 shows an exemplary embodiment of a transfer apparatus 460. The transfer apparatus 460, as shown in FIG. 7, includes a movable surface 465 that includes 3 sets of belts 362, 364, 366. Each set of belts 362, 364, 366 includes three individual belts 362a, 362b, 362c, 364a, 364b, 364c, 366a, 366b, 366c. The first conveyor 460 may also includes one or more raised pads 390, 391, 392. The raised pads 390, 391, 392 may be configured (e.g., sized and positioned) to receive the leading end and/or trailing end of an article. In certain embodiments, the surface of one or more of the raised pads 390, 391, 392 may be configured to provide vacuum suction sufficient to transfer a portion of an article from an first carrier to the raised pad 390, 391, 392. Each raised pad 390, 391, 392 may be joined to a particular set of belts 362, 364, 366 or to one or more of the individual belts 362a, 362b, 362c, 364a, 364b, 364c, 366a, 366b, 366c in a set of belts 362, 364, 366. For example, raised pad 390 may be joined to one or more of the belts 364a, 364b, 364c included in belt set 364. In certain embodiments, each set of belts 390, 391, 392 may include two or more raised pads (e.g., 3, 4, or more, depending on the cycle desired for each set of belts 362, 364, 366). The raised pads 390, 391, 392 may be configured such that each raised pad 390, 391, 392 travels with its respective belt set 362, 364, 366 without interfering with the movement of the other belts and/or raised pads. For example, raised pad 390 may be joined to belt set 364 such that it travels in the MD at the same speed as the belts 364a, 364b, 364c in the set but does not undesirably interfere with the movement of the other belts 362a, 362b, 362c, 366a, 366b, and/or 366c, which may be travelling at the same or a different speed. In certain embodiments, the raised pads 390, 391, 392 may be configured to accommodate articles of different widths, for example, by providing raised pads 362, 364, 366 that have a particular width and/or position in the CD. The movable surface of the transfer apparatus may be driven by one or more variable speed motors such as one of the servo motors exemplified above. In certain embodiments, each set of belts 362, 364, 366 may be mechanically coupled to a separate motor, e.g., via a shaft and one or more drive pulleys. Each shaft may include one or idler pulleys that permit one or more of the belts not driven by the shaft to freely rotate around the shaft.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for transferring articles in a machine direction from a first carrier moving at a first speed to a second carrier moving at a second speed greater than the first speed, each article having a leading end and a trailing end, the method comprising:

transferring the leading end of each article from the first carrier to a first transferring surface configured to receive the leading end of each article from the first carrier, the first transferring surface being mechanically coupled to a first drive motor that advances the first transferring surface in the machine direction towards the second carrier;

advancing the first transferring surface at the first speed as the leading end of each article is transferred from the first carrier to the first transferring surface;

decelerating the first transferring surface to accumulate slack in the article;

transferring the trailing end of each article to a second transferring surface configured to receive the trailing end of each article from the first carrier, the second transferring surface being mechanically coupled to a second drive motor that advances the second transferring surface in the machine direction;

advancing the second transferring surface at the first speed as the trailing end of each article is transferred from the first carrier to the second transferring surface;

accelerating the first transferring surface to the second speed before the leading end of the article is transferred to the second carrier;

accelerate the second transferring surface to the second speed before the trailing end of each article is transferred to the second carrier;

transferring the leading end of each article to the second carrier; and transferring the trailing end of each article to the second carrier.

2. The method of claim 1, wherein the accumulated slack is completely removed when the leading end is transferred to the second carrier.

3. The method of claim 1, wherein at least one of the first and second transferring surfaces include at least one belt.

4. The method of claim 1, wherein the first transferring surface applies a peel force to the leading end of the article to transfer the leading end from the first carrier to the first transferring surface.

5. The method of claim 1, wherein at least one of the first and second drive motors is a programmable servo motor.

6. The method of claim 1, wherein the first transfer surface is accelerated to the second speed before the trailing end is transferred from the first carrier to the second transfer surface.

7. The method of claim 1, wherein the leading end is transferred to a raised pad disposed on the first transferring surface.

* * * * *